United States Patent [19]

Johnson

[11] Patent Number: 4,998,920

[45] Date of Patent: Mar. 12, 1991

[54] PROTECTIVE ASSEMBLY FOR HYPODERMIC SYRINGE DEVICES

[76] Inventor: Delores Johnson, 6920 Summerfield Dr., Indianapolis, Ind. 46214

[21] Appl. No.: 421,119

[22] Filed: Oct. 11, 1989

[51] Int. Cl.⁵ .............................................. A61M 5/32
[52] U.S. Cl. ..................................... 604/198; 604/263
[58] Field of Search ................ 604/198, 263, 187, 192

[56] References Cited

U.S. PATENT DOCUMENTS

| 3,890,971 | 6/1975 | Leeson et al. | |
| 4,356,822 | 11/1982 | Winstead-Hall | |
| 4,573,976 | 3/1986 | Sampson et al. | 604/198 |
| 4,631,057 | 12/1986 | Mitchell | 604/198 |
| 4,639,249 | 1/1987 | Larson | 604/198 |
| 4,655,751 | 4/1987 | Harbaugh | 604/198 |
| 4,675,005 | 6/1987 | DeLuccia | 604/110 |
| 4,681,567 | 7/1987 | Masters et al. | 604/198 |
| 4,702,739 | 10/1987 | Milorad | 604/198 |
| 4,737,144 | 4/1988 | Choksi | 604/198 |
| 4,737,150 | 4/1988 | Baeumle et al. | 604/198 |
| 4,738,663 | 4/1988 | Bogan | 604/198 |
| 4,743,233 | 5/1988 | Schneider | 604/198 |
| 4,747,829 | 5/1988 | Jacob et al. | 604/110 |
| 4,747,830 | 5/1988 | Gloyer et al. | 604/110 |
| 4,747,831 | 5/1988 | Kulli | 604/110 |
| 4,747,836 | 5/1988 | Luther | 604/198 |
| 4,752,290 | 6/1988 | Schramm | 604/198 |
| 4,755,170 | 7/1988 | Golden | 604/52 |
| 4,758,231 | 7/1988 | Haber et al. | 604/198 |
| 4,772,272 | 9/1988 | McFarland | 604/198 |
| 4,775,369 | 10/1988 | Schwartz | 604/263 |
| 4,775,376 | 10/1988 | Strung | 604/415 |
| 4,778,453 | 10/1988 | Lopez | 604/110 |
| 4,790,827 | 12/1988 | Haber et al. | 604/198 |
| 4,795,432 | 1/1989 | Karczmer | 604/110 |
| 4,795,443 | 1/1989 | Permenter et al. | 604/198 |
| 4,810,248 | 3/1989 | Masters et al. | 604/192 |
| 4,813,940 | 3/1989 | Parry | 604/198 |
| 4,816,022 | 3/1989 | Poncy | 604/198 |
| 4,826,488 | 5/1989 | Nelson et al. | 604/192 |

Primary Examiner—John D. Yasko
Attorney, Agent, or Firm—Willian Brinks Olds Hofer Gilson & Lione

[57] ABSTRACT

A protective assembly is provided for adaptation to conventional hypodermic syringe devices or to be made as an integral part of such devices upon their manufacture. The protective assembly includes a sleeve member and collar member. The sleeve member is adapted to be arranged circumjacent the syringe barrel and the collar member is adapted to be affixed to the syringe barrel adjacent the needle. The sleeve member threadably communicates with the collar member when the sleeve member is moved axially between a first retracted position in which the needle is exposed toward a second extended position in which the needle is covered. A securing means is provided by which the sleeve member may be permanently secured in the extended position so as to prevent inadvertent sticks by the needle as well as the reuse of the contaminated needle.

12 Claims, 1 Drawing Sheet

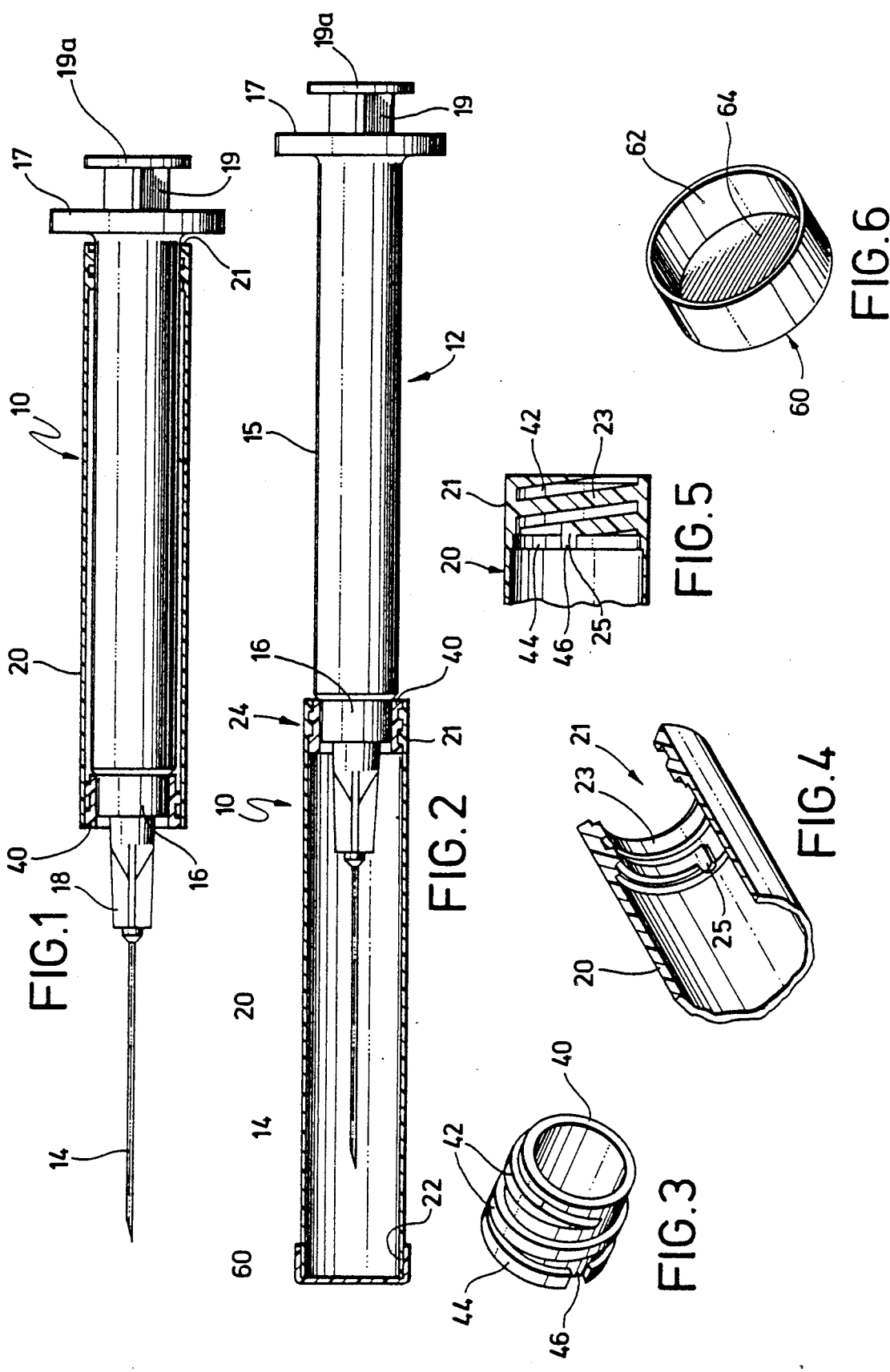

PROTECTIVE ASSEMBLY FOR HYPODERMIC SYRINGE DEVICES

TECHNICAL FIELD

This invention relates to hypodermic syringe particularly, relates to protective assemblies for use with such devices which prevent the user from being advertently stuck by a contaminated injection needle as well as preventing its reuse.

BACKGROUND ART

Devices for injecting a medication into a body or for aspirating a fluid, such as blood, from a body of a human or animal patient are well known. Such a device commonly includes a syringe barrel which can retain a quantity of medication or other injectant, and an intravenous or subcutaneous needle which is inserted into the skin of the patient for administration of a medication or aspiration of a fluid. These devices are generally of the disposable nature and hence are normally discarded after a single use.

It is common practice after the administration of an injection or the aspiration of fluids from a patient in which a conventional syringe is used for the user to replace a molded sheath or scabbard on the exposed contaminated needle to prevent inadvertent puncture wounds from the needle point, or to merely lay the syringe down upon a surface leaving the contaminated needle exposed. Replacement of the needle sheath is dangerous as such sheaths tend to be small in diameter thus requiring a concentrated effort to align the point of the needle with the opening of the sheath prior to sliding the sheath over the needle. Such occurrences often result in a person being inadvertently pricked or stuck by the contaminated needle.

Injury by accidental needle sticks has been recognized as a serious health hazard and the danger of exposure to fatal blood-transmitted viruses, such as hepatitis, herpes, and of must recent concern, acquired immunodeficiency syndrome (AIDS), through accidental pricks by a contaminated injection needle is well documented. Medical research has confirmed that the slightest prick or puncture of the skin by a contaminated needle may communicate the contaminating virus to the injured party. In addition, the syringe is normally discarded after a single use and if the contaminated needle remains exposed, this danger of exposure is likewise presented to those handling and disposing of the medical refuse.

One approach to this problem has been to provide a tubular cover or sleeve that can be slid downwardly over the needle after its use to shield the needle and prevent inadvertent contact therewith. Such prior attempts include syringe devices having a slidable sheath or sleeve member mounted thereon adapted to reciprocably and axially move over the syringe barrel and engaging means by which the sheath or sleeve may be fixed in a desired position. For example, a common embodiment of such an assembly includes a fixed guide lug which travels within a longitudinal slot or groove formed in the sheath so that the sheath can be moved to selectively cover or expose the needle. Examples of such inventions are presented in the following U.S. Pat. Nos.: 4,425,150 to Sampson, et al.; 4,643,199 to Jennings, Jr., et al.; 4,643,200 to Jennings, Jr.; 4,693,708 to Wanderer, et al.; and 4,702,738 and 4,723,943 to Spencer.

U.S. Pat. No. 4,743,233 to Schneider presents another prior attempt which provides a safety cap syringe generally comprising a safety sleeve mounted adjacent the syringe barrel and which extends axially to shroud the needle. In one embodiment of Schneider, the threaded barrel is provided with a threaded portion formed at its external surface adjacent the needle and the safety sleeve is provided with a pair of corresponding threaded portions formed at its internal surface, one threaded portion arranged adjacent the proximal end of the sleeve and the other adjacent the distal end. When the protective sleeve is moved to the closed or extended position, the proximal threaded portion of the sleeve threadably engages the threaded portion formed on the syringe barrel to releasably secure the safety sleeve in the extended position. By rotating the sleeve, the sleeve may be disengaged from the syringe barrel threads and thereafter slidably moved along the syringe barrel to expose the needle, at which point the sleeve is rotated again to threadably engage the distal threaded portion of the sleeve with the threaded portion provided on the syringe barrel, thereby releasably securing the safety sleeve in the open position so that the syringe is ready for use. Schneider provides no means, however, by which the safety sleeve may be permanently secured in the extended position. Such a feature is essential in preventing reuse of the contaminated needle and inadvertent puncture wounds caused by an exposed needle.

Furthermore, the absence of a permanent locking means in Schneider can prove hazardous as medical personnel often will not take or do not have sufficient time to screw the safety shield completely into position. For example, in emergency situations, a medical personnel may simply rotate the safety shield only a few rotations to engage the corresponding threaded portions, thereby making it possible during subsequent handling and jostling for the safety shield to become disengaged and move axially over the syringe barrel, thereby exposing the contaminated needle and representing the dangerous hazard.

Moreover, the safety sleeve and the pair of like threaded portions provided by Schneider are manufactured as an integral component of the safety-cap syringe. This arrangement complicates the manufacturing process involved as well as increasing its cost.

There has developed a definite need for a practical, inexpensive and simple solution to the problem of inadvertent injuries caused by contaminated needles during the handling of hypodermic syringe devices.

DISCLOSURE OF THE INVENTION

In accordance with a presently preferred embodiment of the invention, a novel assembly is provided which includes a protective cover or sleeve member which is adapted to be slidably mounted on a conventional syringe barrel and which may be secured in an extended position to shield or shroud the point of the injection needle. The protective sleeve is reciprocably movable between a first retracted position in which the point of the injection needle is fully exposed to effect the injection or aspiration of fluids, and a second extended position in which the point of the needle is located within the sleeve, thereby providing a protecting covering about the needle to prevent accidental contact therewith.

The protective assembly provided by this invention further includes an externally threaded collar member which is adapted to be arranged circumjacent the distal end of the syringe barrel adjacent the intravenous needle. The protective sleeve is provided with a mating internally threaded portion arranged at its proximal end. The internally threaded portion is adapted to engage the externally threaded collar as the sleeve is moved axially from the first retracted position toward the second extended position and, upon relative rotation between the sleeve and the syringe barrel, secure the sleeve in the extended position.

In addition, the internally threaded portion of the sleeve includes means for fixedly securing the sleeve member in the extended position, preferably a locking tab or dog protrusion which, as the sleeve is being rotated about the syringe barrel and approaches its maximum point of rotation, aligns with and is received by a slot or cavity formed in the externally threaded collar, thereby preventing any further rotational or longitudinal movement of the sleeve and permanently securing the sleeve in the extended position. The sleeve can now only be retracted to expose the needle by destroying or substantially damaging the structure of the protective assembly.

A cap is preferably provided by this invention adapted to be placed on the open distal end of the sleeve when in the extended position to prevent any access to the needle point and to fully enclose the needle within the sleeve.

The simple structure of the protective syringe assembly comprises merely the sleeve member and the externally threaded collar. This simple and inexpensive structure renders it adaptable to be used in conjunction with various existing syringe devices, or available for manufacture as an integral component of such devices.

After the sleeve has been securely fixed in the extended position, it is virtually impossible for accidental needle sticks to occur or for the contaminated needle to be reused. Previous attempts to develop such a simple and inexpensive protective syringe assembly such as provided by this invention have not been successful to date. Further features of the invention will be apparent from the following drawings and disclosure of the preferred embodiment of the invention.

BRIEF DESCRIPTION OF THE DRAWINGS

FIG. 1 is a side elevation view in section of a protective assembly provided by this invention mounted on a standard hypodermic syringe device with the protective sleeve in a retracted position;

FIG. 2 is the protective assembly of FIG. 1 with the sleeve in an extended position;

FIG. 3 is a perspective view of the externally threaded collar member provided by this invention;

FIG. 4 is a fragmentary perspective view of the outer body of the protective sleeve showing a partial view of the internally threaded portion of the protective sleeve;

FIG. 5 is a partial side elevation cross-sectional view illustrating the securing means provided by this invention while the protective sleeve is in the extended position; and FIG. 6 is a perspective view of a cap that may be employed with the protective assembly provided by this invention.

BEST MODE FOR CARRYING OUT THE INVENTION

A protective assembly 10 provided in accordance with this invention is shown in FIGS. 1 and 2 mounted upon a standard syringe device 12. Protective assembly 10 comprises a protective sleeve or sheath 20 and an externally threaded collar member 40. Collar 40 is adapted to be mounted onto barrel 15 at distal end 16 adjacent injection needle 14 and needle hub 18. A protective cap 60 is preferably employed which may be placed over open distal end 22 when the sleeve 20 is in the extended position.

Syringe device 12 is a type commonly available and comprises a barrel 15, a flanged portion 17, needle hub 18 which couples injection needle 14 with an inner chamber provided in barrel 15, and a plunger 19 having a finger-receiving portion 19A. As is commonly known, plunger 19 is adapted to move reciprocably within syringe barrel 15 to inject fluids retained in barrel 15 out through injection needle 14, or to aspirate fluids into the syringe barrel through injection needle 14, as desired. Although not shown in FIGS. 1 and 2, syringe device 12 includes an elastomeric member affixed to the end of rod 19 opposite finger-receiving portion 19a. The elastomeric member is generally similar to a piston head and provides a fluid-tight seal or interface with the surface of the inner chamber of barrel 15 so as to effect the injection or aspiration of fluids.

Protective sleeve 20 is provided with an internally threaded portion 21 (FIG. 4) arranged at proximal end 24. Collar 40, most clearly shown in FIG. 3, is arranged on the distal end of barrel 15 opposite flanged portion 17 and is adapted to threadably communicate with internally threaded portion 21 when the sleeve is moved axially from the first retracted position shown in FIG. 1 toward the second extended position shown in FIG. 2. Collar 40 includes external threads 42, stop ring 44 and locking slot or cavity 46. Internally threaded portion 21 of sleeve 20 is more clearly shown in FIG. 4 as including internal threads 23 and locking tab or dog protrusion 25. Locking slot or cavity 46 and locking tab or dog protrusion 25 comprise means for fixedly securing protective sleeve 20 in the desired extended position.

In use, sleeve 20 is retracted so as to expose the injection needle to effect an injection or aspiration. Thereafter, sleeve 20 is slidably moved from the first retracted position toward the second extended position until internally threaded portion 21 engages collar 40, at which point sleeve 20 is rotated relative to barrel 15 so that portion 21 and collar 40 threadably communicate to secure sleeve 20 in the protecting extended position shown in FIG. 2. Sleeve 20 may be provided with splined or serrated gripping surfaces (not shown) arranged at its external surface to facilitate its movement by the user.

The threading engagement between portion 21 and collar 40 is more clearly shown in FIG. 5 wherein sleeve 20 has been theretofore rotated so that internal threads 23 of the sleeve have threadably engaged external threads 42 of the collar until tab 25 has come into alignment with slot 46 provided in stop ring 44. At this point, locking tab 25 is received in locking slot 46, thereby preventing further rotational or longitudinal movement of sleeve 20 and permanently securing the sleeve in the protecting extended position. Once locking tab 25 is securely received in slot 46, one can only retract protective sleeve 20 by damaging or destroying the structure of the protective assembly, i.e., portion 21 or collar 40. Hence, after its use, needle 14 is protected without having to replace a needle cap or scabbard and without requiring the user to come in contact with the contaminated needle, both of which may prove hazardous to the user.

Protective cap 60 is shown in FIG. 6 comprising annular ring 62 attached to transverse wall 64. Protective cap 60 may be optionally employed over the open distal end 22 of sleeve 20 to provide essentially a full enclosure for injection needle 14, thereby preventing any access or inadvertent contact with the contaminated needle.

Sleeve 20 is preferably transparent to allow the user to view the fluid contents contained in barrel 15 and any graduated volumetric markings commonly appearing on such syringe barrels. Alternatively, the sleeve may be provided with a window(s) (not shown) as means to view the barrel and/or its contents.

As may be distilled from the above discussion, protective assembly 10 provided by this invention may be employed with an existing standard syringe device simply by placing sleeve 20 over the barrel of the syringe device and affixing or bonding collar 40 to the syringe barrel using conventional adhesive means. It is foreseen that syringe barrels of different makes may be of varying diameters; consequently, collar 40 and sleeve 20 may be manufactured in varying sizes to accommodate variations in syringe dimensions.

The protective sleeve provided by this invention is preferably manufactured from plastic materials of the type ordinarily used for the manufacture of hypodermic syringe devices. Such a material may include any acrylic, polyethylene, PVC, polypropylene, nylon or other like material which can be formed into the desired shape. An injection molding process is a preferred manufacturing method although other forming methods can be employed.

As noted, a large portion of the syringe devices employed today are of the disposable nature and are used with patients having blood-transmittable viruses, such a hepatitis, herpes or AIDS. It is therefore essential that once the syringe device is used and the injection needle becomes contaminated, that the syringe device and contaminated needle be disposed of properly and that nothing come in contact with the contaminated needle, including object, user or patient. The protective assembly provided by the preferred embodiment of this invention accomplishes this desired result.

In addition, in view of the disposable nature of a majority of the syringe devices employed today, a minimal cost to manufacture the device is essential. The simple structure of the protective assembly provided by this invention, as well as it minimal number of parts (e.g., protective sleeve and collar) achieve this further desired result.

This invention substantially prevents the inadvertent sticks and puncture wounds caused by injection needles as well as the hazards of blood-transmitted viruses resulting from such mishaps. A further advantage provided by this invention is that once the protective sleeve has been permanently secured in the extended position, the syringe may not be used again, thereby preventing the mistaken use of a contaminated injection needle and reducing the likelihood of transmission of life-threatening viruses.

Thus, the present invention provides the protective assembly as represented in the preferred embodiment shown in FIG. 1-6. It must be understood, however, that there are other embodiments and variations of the invention that may be developed and that the invention is not restricted to the preferred embodiment and mode of operation currently understood and described herein, but is only limited by the scope of the following claims.

I claim:

1. A syringe device comprising:
   a syringe barrel adapted to retain a fluid therein, the barrel having an open proximal end and an opposing distal end, the distal end having an orifice formed therein, the orifice being adapted to communicate with a tubular needle through which fluid is passed;
   plunger means adapted to be carried within the barrel and defining an inner chamber therein in which fluid is retained, the plunger means being adapted to move reciprocably within the barrel to effect the passing of fluid into or out of the inner chamber through said orifice;
   an externally threaded collar member adapted to be mounted on the barrel adjacent the distal end of the barrel and having a slot formed as an integral part thereof;
   a protective sleeve member adapted to be arranged circumjacent the barrel, the sleeve member having an inner diameter greater than the outer diameter of the barrel so as to allow the sleeve member to move axially about the barrel, the sleeve member having an open proximal end and an open distal end and an internally threaded portion disposed adjacent the proximal end, said internally threaded portion being adapted to threadably engage said externally threaded collar member and having a tab formed as an integral part thereof, said slot and said tab being arranged substantially transversely to the direction of intended rotation;
   means for fixedly securing the sleeve member in a desired position, said securing means being defined by the tab of the internally threaded portion and the slot of the externally threaded portion,
   the sleeve member being adapted to be moved axially from a first retracted position in which the needle is sufficiently exposed to effect the injection or aspiration of fluid to a second extended position in which the needle is located within the sleeve member, the sleeve member being adapted to move axially and rotatably so that the internally threaded portion of the sleeve member engages the externally threaded collar member, the rotation of the sleeve member relative to the barrel eventually aligning the tab with the slot whereat the tab enters and is received by the slot, thereby preventing further rotational or longitudinal movement of the sleeve member relative to the barrel and fixedly securing the sleeve member in the second extended position where the distal end of the sleeve member extends beyond the needle to prevent inadvertent contact therewith.

2. The syringe device as in claim 1 further comprising a detachable cap member which is adapted to be arranged on the distal end of the sleeve member when the sleeve member is secured in the second extended position.

3. The syringe device as in claim 1 wherein the plunger means comprises an elastomeric member and a rod member, the elastomeric member being affixed to the rod member and having an outer diameter slightly less than the inner diameter of the barrel so as to allow the elastomeric member to move reciprocably therewithin while still providing a fluid-tight seal therebetween and wherein the motion of the rod member being effected by moving the rod member so as to expel fluids from within the inner chamber when moving the rod member in one direction and to aspirate fluids into the inner chamber when moving the rod member in an opposite direction.

4. The syringe device as in claim 3 wherein the rod member is provided with a finger-receiving portion disposed at the end opposite the elastomeric member, the finger-receiving portion being arranged transversely to the longitudinal axis of the rod member to effect movement of the plunger means by finger pressure being applied thereto.

5. The syringe device as in claim 1 wherein the barrel is provided with graduated indicia appearing thereon.

6. The syringe device as in claim 1 wherein the sleeve member is comprised of transparent material.

7. The syringe device as in claim 1 wherein the barrel and the sleeve member each have a cylindrical shape.

8. A protective assembly adapted to be mounted on a hypodermic syringe device, the hypodermic syringe device comprising a barrel member, a plunger means and an injection needle, the barrel member having an open proximal end and an opposing distal end, the distal end having an orifice formed therein through which fluid flows to and from said needle, the plunger means being carried within the barrel member and movable reciprocably therewithin to inject or aspirate fluids, the protective assembly comprising:

an externally threaded collar member having a cavity formed as an integral part thereof and arranged substantially transversely to the intended direction of rotation, said collar member being adapted to be mounted onto the barrel member adjacent the distal end of the barrel member; and a protective sleeve member adapted to be arranged circumjacent the barrel member, the sleeve member having an inner diameter greater than the outer diameter of the barrel so as to be movable axially thereabout between a first retracted position in which the point of the needle is sufficiently exposed to effect the injection or aspiration of fluids and a second extended position in which the point of the needle is located within the protective sleeve member, the sleeve member having an internally threaded portion arranged adjacent the proximal end of the sleeve member, said internally threaded portion being provided with a dog protrusion formed as an integral part thereof extending substantially transversely to the direction of intended rotation, the sleeve member being adapted to be moved axially from the first retracted position toward the second extended position until the internally threaded portion of the sleeve member threadably engages the externally threaded collar member whereat the sleeve member is adapted to be rotated about the barrel member until the dog protrusion aligns with the cavity and is received therein, thereby preventing further rotational or longitudinal movement of the sleeve member relative to the barrel member and permanently securing the sleeve member in the second extended position to prevent inadvertent contact with the needle or the reuse of the needle.

9. The protective assembly as in claim 8 further comprising a cap, the cap being adapted to be placed over the open distal end of the sleeve member when the sleeve member is in the second extended portion, thereby enclosing the needle point within the protective assembly.

10. The protective assembly as in claim 8 wherein the barrel is provided with graduated indicia appearing thereon.

11. The protective assembly as in claim 8 wherein the sleeve member is comprised of transparent material.

12. The protective assembly as in claim 8 wherein the barrel and the sleeve member each have a cylindrical shape.

* * * * *

UNITED STATES PATENT AND TRADEMARK OFFICE
CERTIFICATE OF CORRECTION

PATENT NO. : 4,998,920

DATED : March 12, 1991

INVENTOR(S) : Delores Johnson

It is certified that error appears in the above-identified patent and that said Letters Patent is hereby corrected as shown below:

In col. 1, lines 7-8, delete "particularly," and insert therefor --devices used to aspirate or inject fluids, and more particularly,--.

Signed and Sealed this

Eighth Day of September, 1992

Attest:

DOUGLAS B. COMER

*Attesting Officer*     *Acting Commissioner of Patents and Trademarks*